US00PP26196P3

(12) United States Plant Patent
Growns

(10) Patent No.: US PP26,196 P3
(45) Date of Patent: Dec. 8, 2015

(54) WAXFLOWER PLANT NAMED 'WX 74'

(50) Latin Name: ***Interspecific Chamelaucium* hybrid *(Chamelaucium megalopetalum×Chamelaucium uncinatum).***
Varietal Denomination: WX 74

(71) Applicant: Western Australian Agriculture Authority, Bentley (AU)

(72) Inventor: Digby Growns, Kings Park (AU)

(73) Assignee: Western Australian Agriculture Authority, Bentley (AU)

( * ) Notice: Subject to any disclaimer, the term of this patent is extended or adjusted under 35 U.S.C. 154(b) by 143 days.

(21) Appl. No.: 13/987,924

(22) Filed: Sep. 16, 2013

(65) Prior Publication Data

US 2014/0082789 P1 Mar. 20, 2014

Related U.S. Application Data

(60) Provisional application No. 61/744,178, filed on Sep. 19, 2012.

(51) Int. Cl.
*A01H 5/00* (2006.01)
*A01H 5/02* (2006.01)

(52) U.S. Cl.
USPC ..... Plt./226
CPC ..... *A01H 5/02* (2013.01)

(58) Field of Classification Search
USPC ..... Plt./226
See application file for complete search history.

(56) References Cited

PUBLICATIONS van der Ploeg, R., "Exciting developments in waxflower breeding and marketing," Sep. 2011; www.FloraCultureInternational.com- file retrieval on Mar. 28, 2015 (3 pages total).*
www.wafex.com.au/pp./about_wafex/news/2011-09; summary of "Exciting developments in waxflower breeding and marketing," Monday, Sep. 5, 2011; file retrieval on Mar. 30, 2015 (1 page total).*
"New waxflower varieties released," Australian Flower Industry; Sep. 2011; file retrieval on Mar. 30, 2015 (1 page total).*
www.wafex.com.au/pages/about_wafex/news/2011-09; summary of "New waxflower varieties released," Thursday, Sep. 1, 2011; file retrieval on Mar. 30, 2015 (1 page total).*

* cited by examiner

*Primary Examiner* — Susan McCormick Ewoldt
(74) *Attorney, Agent, or Firm* — Michelle Bos Legal LLC

(57) ABSTRACT

'WX 74' is a new and distinct waxflower plant (interspecific *Chamelaucium* hybrid) notable for its foliage that remains green, mid-season flowering, open growth habit, and dense terminal cover of medium-large white flowers that age to white.

6 Drawing Sheets

Latin name of the genus and species of the plant claimed: Interspecific *Chamelaucium* hybrid (*Chamelaucium megalopetalum×Chamelaucium uncinatum*).
Variety denomination: 'WX 74'.

BACKGROUND OF THE INVENTION

'WX 74' is a new waxflower plant that originated as a seedling produced in a sexual breeding program conducted by the breeder at Medina and South Perth, Western Australia. 'WX 74' was selected from seedlings of an open pollination. Female parent *Chamelaucium megalopetalum* 'CM12.1-4' (not patented) was pollinated by an unknown male parent, likely *C. uncinatum* 'Alba' (not patented), which was growing in close proximity at Medina, Western Australia. An embryo was excised from resulting fruit produced in August 2000 and germinated in vitro. The resulting seedling was subcultured in tissue culture four times, deflasked, hardened and planted in the field at Medina, Western Australia in May 2001. Following flowering in June 2002, the seedling was vegetatively propagated via cuttings and a second generation of cuttings was taken in 2009 at Medina, Western Australia. Growth and flowering records of the generations were recorded during the period 2002 to 2010. No off types were recorded and all plants were found to be uniform and stable.

'WX 74' is distinguishable from its female parent 'CM 12.1-4' by a number of features, as described in Table 1 below:

TABLE 1

| Characteristic | CM 12.1-4 | WX 74 |
|---|---|---|
| Flower diameter | Large | Medium |
| Plant height | Short | Medium-tall |
| Flower arrangement of petals | Touching | Free |
| Flower colour | White aging to red | White aging to white |

'WX 74' is distinguishable from its presumed male parent 'Alba' by a number of features, as described in Table 2 below:

TABLE 2

| Characteristic | Alba | WX 74 |
|---|---|---|
| Leaf length | Long | Small-medium |
| Leaf cross section | Rounded | Flattened triangular |
| Flower attitude of petals | Horizontal | Semi-erect |
| Pedicel length | Medium-long | Small-medium |

'WX 74' is also distinguishable from other known waxflower varieties. Comparisons of 'WX 74' to 'Crystal Pearl'

(not patented) and 'Ivory Pearl' (not patented), the most similar varieties of common knowledge, are set forth in Tables 3 and 4 below:

TABLE 3

| Characteristic | Crystal Pearl | WX 74 |
|---|---|---|
| Leaf length | Medium | Short |
| Leaf cross-section | Flattened/round | Flattened/triangular |
| Pedicel length | Medium to long | Short to medium |
| Time of beginning of flowering | Early | Medium |

TABLE 4

| Characteristic | Ivory Pearl | WX 74 |
|---|---|---|
| Leaf length | Long | Short |
| Leaf cross-section | Round | Flattened/triangular |
| Lear colour | Green turning to yellow | Green |
| Flower diameter | Medium to large | Medium |
| Pedicel length | Medium to long | Short to medium |

BRIEF DESCRIPTION OF THE PHOTOGRAPHS

The accompanying photographs show four-year-old 'WX 74' waxflower plants growing at Medina, Western Australia during August and September (early spring) 2013.

DETAILED BOTANICAL DESCRIPTION

Figure 1:
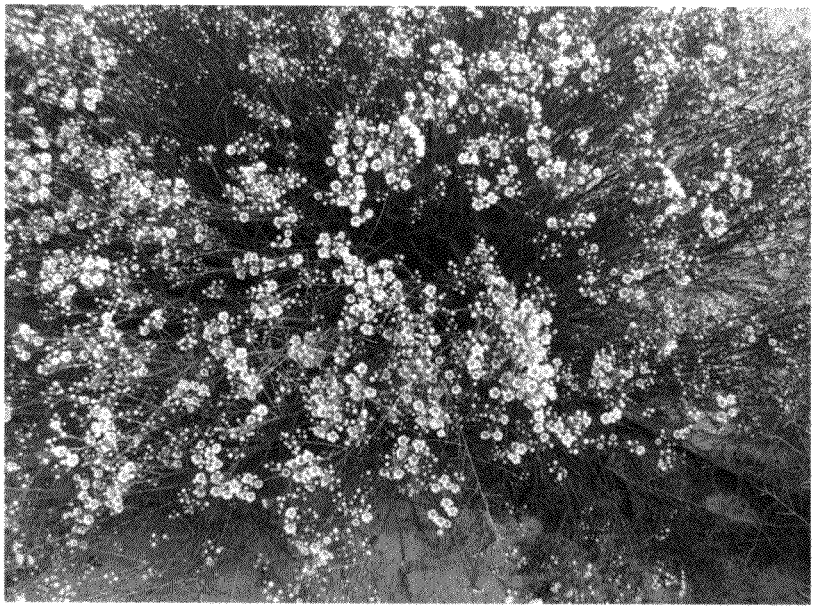
FIG. 1 is a photograph of 'WX 74' growing outdoors.
Figure 2:
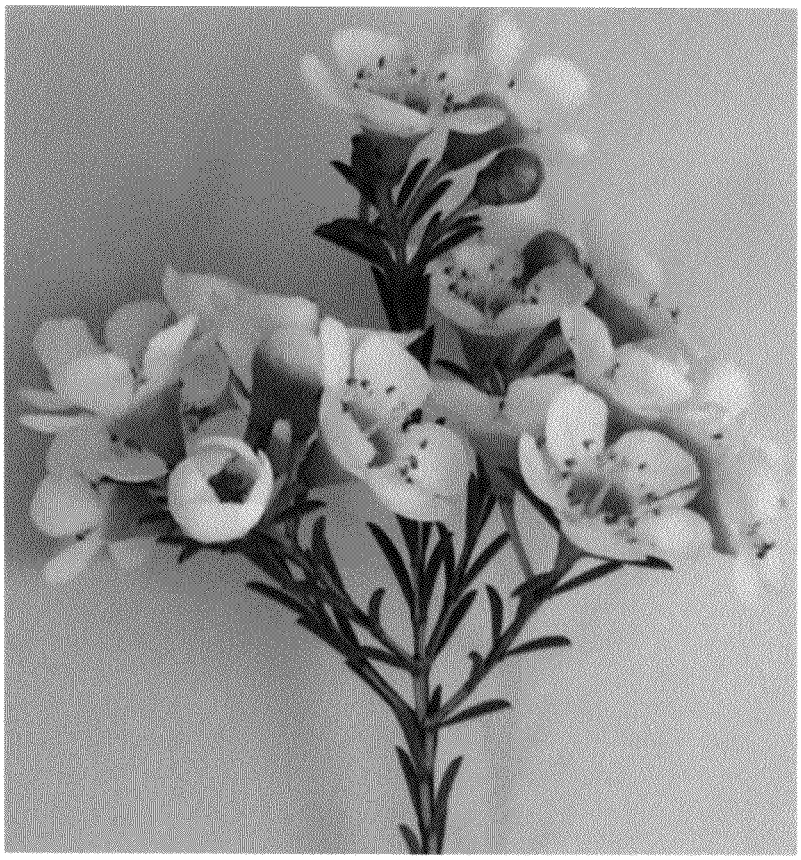
FIG. 2 is a photograph of a sprig of leaves and flowers of 'WX 74'.
Figure 3:
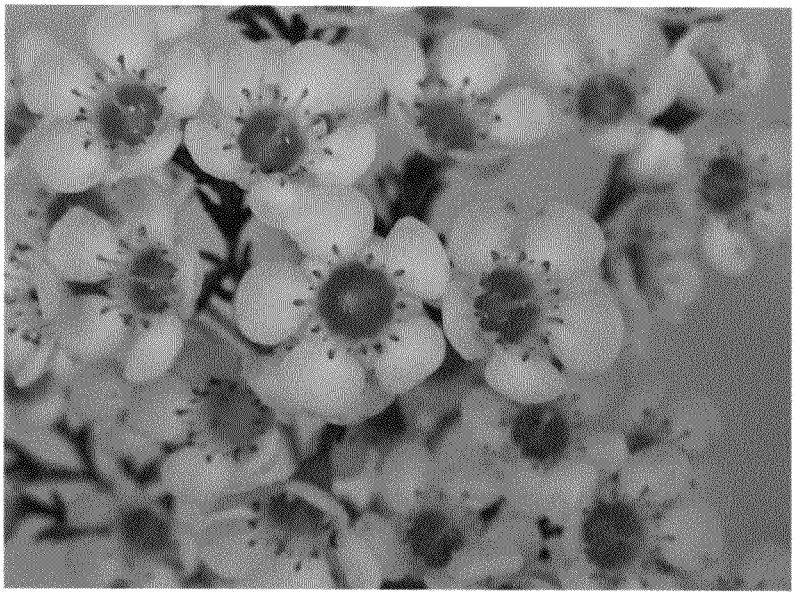
FIG. 3 is a close-up photograph of young flowers of 'WX 74'.
Figure 4:
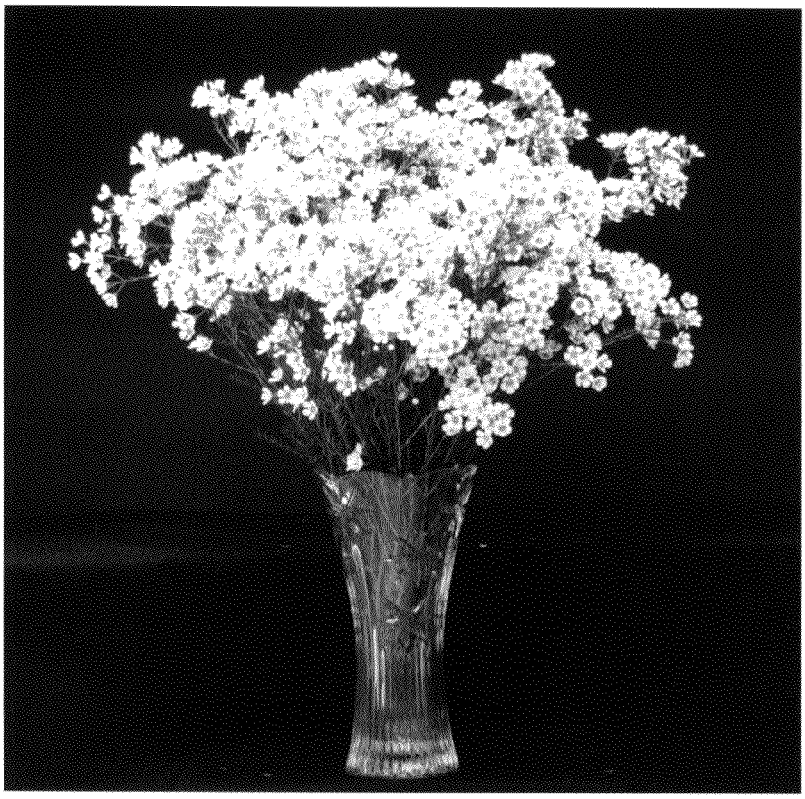
FIG. 4 is a photograph of flowers of 'WX 74'.
Figure 5:
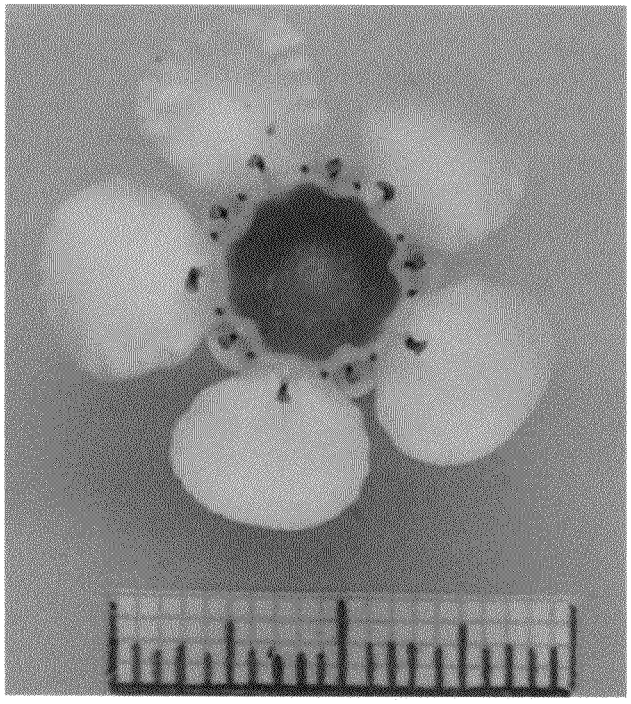
FIGS. 5 and 6 are close-up photographs of flowers of 'WX 74'.
Figure 6:
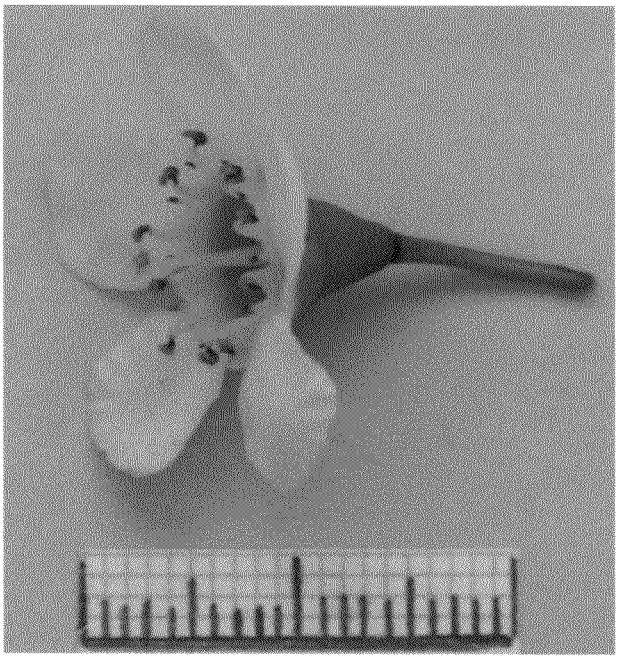
Figure 7:
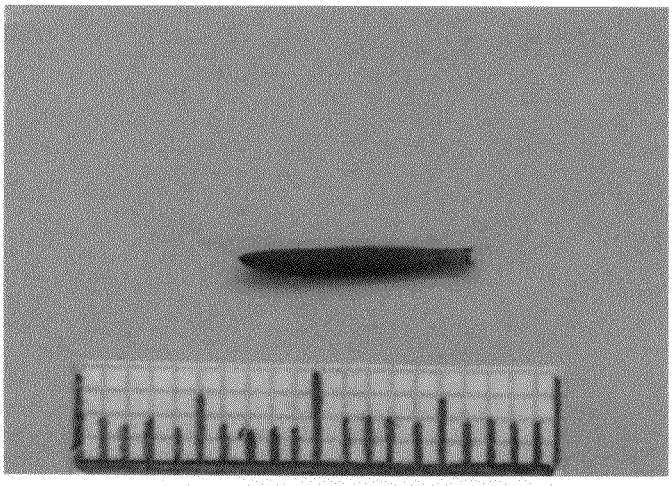
FIG. 7 is a close-up photograph of a leaf of 'WX 74'.
Figure 8:
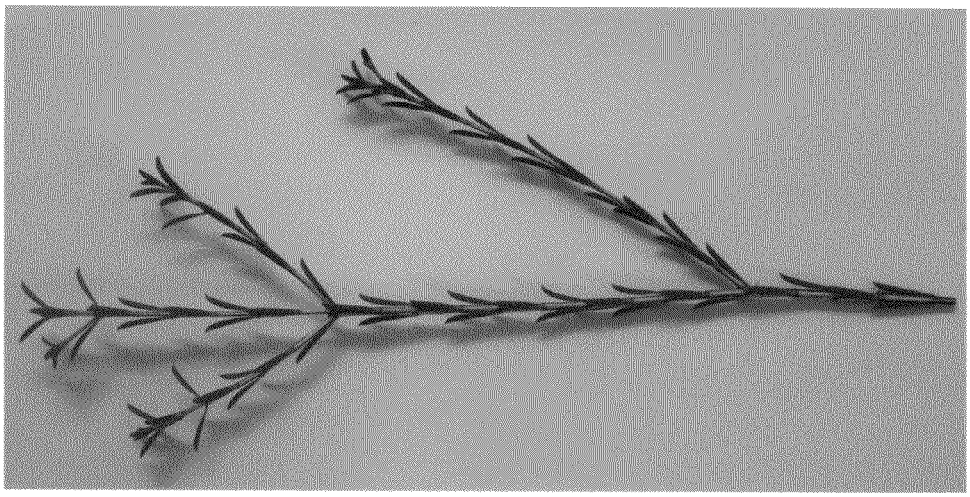
FIG. 8 is a photograph of a branch and leaves of 'WX 74'.
Figure 9:
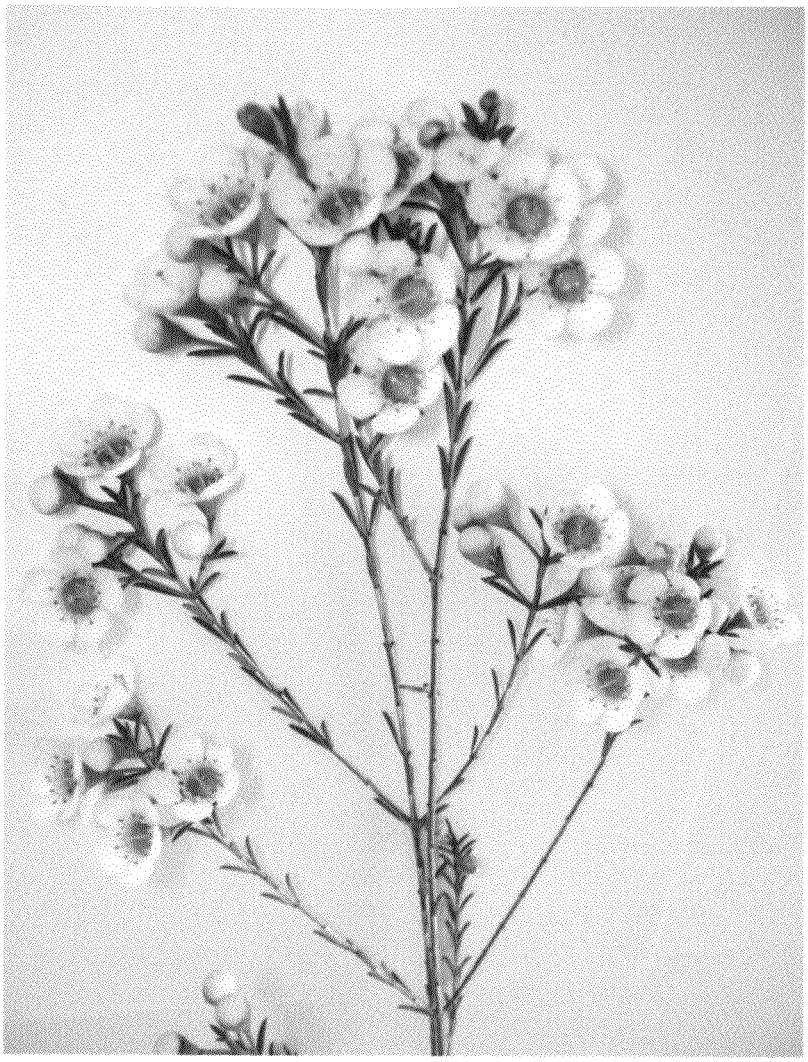
FIG. 9 is a photograph of a stem of leaves and flowers of 'WX 74'.
Figure 10:
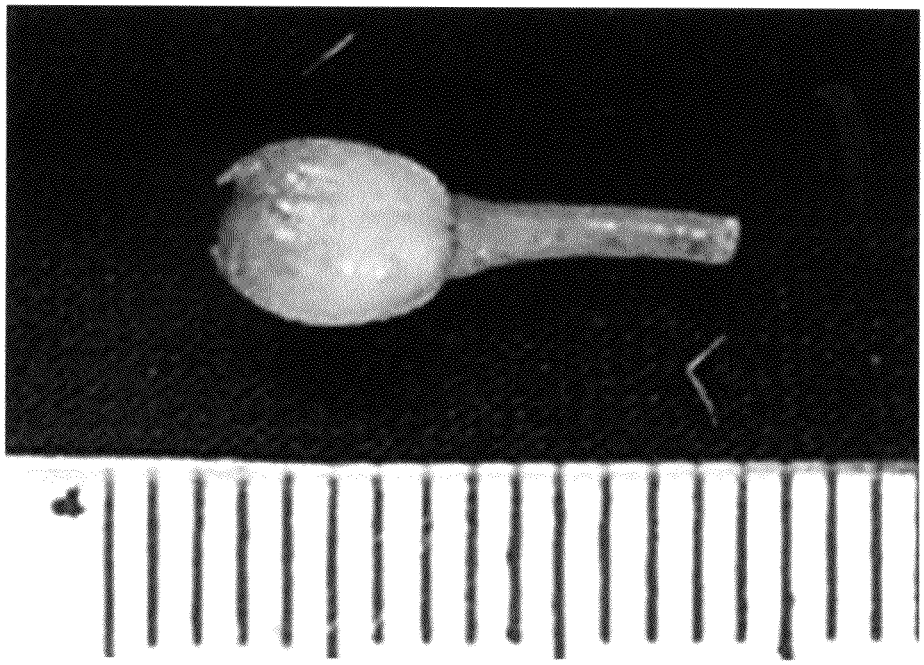
FIG. 10 is a close-up photograph of a young bud of 'WX 74'.
Figure 11:
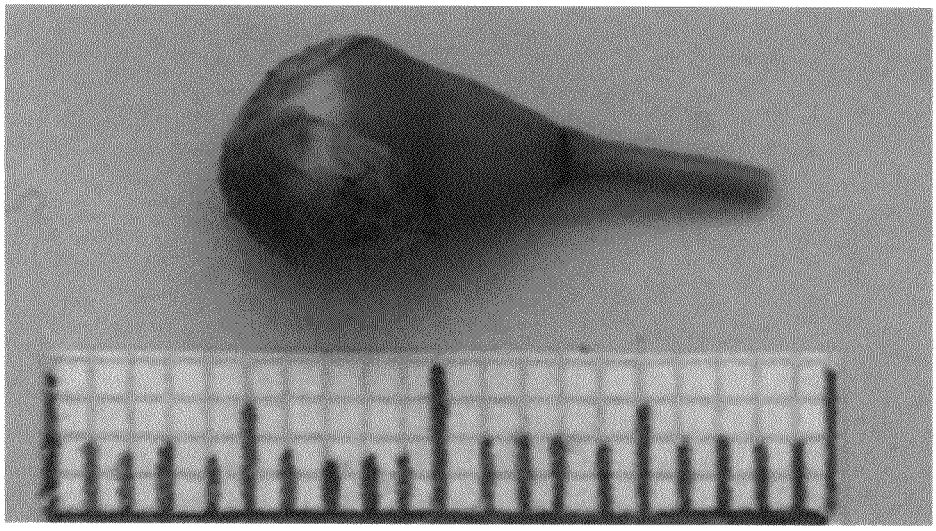
FIG. 11 is a close-up photograph of an older bud of 'WX 74'.

The following detailed botanical description is based on observations of four year old 'WX 74' waxflower plants growing at Medina, Western Australia during August and September (early spring) 2013, except where otherwise noted. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Plant:

*Summary*.—'WX 74' is a mid-season flowering, spreading medium-tall bush with dense terminal cover of medium to large (17 mm) white flowers with yellow-green 151B centers. The petals age to white.

*Growth habit*.—Branching, upright shrub growing to a height of 1.5 m and a bush diameter of 1.5 m.

*Flowering stem length*.—60 to 70 cm.

*Branches*.—Average of 27 main branches per plant; diameter 5.7 mm; round cross-section; smooth texture; color Grey-brown 201A and 201C. (Branch description taken from five-year-old stock plants.)

Leaves:

*Leaf arrangement*.—Opposite.

*Leaf density*.—Main branch: about 6 pairs per 6 cm branch length. Secondary branch: 6 pairs of leaves, branch 5 cm in length.

*Attitude*.—Held at about 25 to 30 degree angle to stem.

*Aroma*.—Eucalyptus or citrus aroma when leaves are crushed.

*Leaf internode length*.—Average 9.0 mm on main branch, and 7.2 mm on secondary branch.

*Leaf size*.—Length 10.5 mm, width 1.4 mm.

*Leaf shape*.—Narrowly obovate with acute apex.

*Leaf surface texture*.—Glabrous glandular, leathery, shiny.

*Leaf margin*.—Entire.

*Leaf base*.—Sessile truncate to stem.

*Leaf cross section*.—Triangular with flat upper surface.

*Leaf color*.—New growth, upper and lower surface yellow-green 144B to 144C; mature leaves, upper and lower surface green N137B.

*Leaf division*.—Simple. Leaf venation — None visible.

Flower:

*Flower bud*.—Fresh buds cone-shaped with smooth shiny surface, color yellow-green 145B, tip of bud orange-red N30; diameter 4.4 mm, length 4.6 mm. Older buds more elongated with papery operculum, coarse, surface color grey-brown N199B to N199C; diameter 4.8 mm, length 9.0 mm.

*Flowering season*.—August (Medina, Western Australia).

*Flower longevity*.—60 days.

*Flower quality*.—High.

*Flowering time*.—Mid-season.

*Flower description*.—Flowers slightly cupped and petals separate, elongated round in shape, upper and lower surface are glabrous waxy, entire margin, truncate base and fused to calyx, rounded apex. Flower color remains constant as it matures (lower and upper surface same coloration).

*Petal color*.—On day of opening, white 155A; When partially developed, petals remain white 155B; When fully developed petals remain white 155C.

*Flower arrangement*.—Corymb.

*Flower type*.—Single flower.

*Flowering habit*.—Terminal, panicle florescence.

*Flower shape*.—Cup-shaped.

*Flower diameter*.—Average 17.9 mm; depth 12.2 mm (top of stigma to bottom of ovary).

*Flowering branch angle*.—Overlapping.

*Flowering attitude of petals on day of opening*.—Semi erect.

*Flowering branch angle 2 weeks after opening*.—Semi-erect.

*Length of sepal in relation to length of petal*.—Less than one-third.

*Petiole (pedicle) length*.—Long, 8.2 mm, aspect 25 degrees to 35 degrees.

*Hypanthium shape*.—Obconical.

*Hypanthium diameter*.—Medium, 7.3 mm.

*Hypanthium main color at middle part on day of opening of flower*.—Yellow-green 145A; 4 weeks after opening of flower yellow-green 145A.

*Nectaries*.—About 6 mm in diameter, color see hypanthium.

*Flower petals*.—5, round shape; fused sepals at base to hypanthium, with rounded outer separate lobes arranged alternately between petals; tube portion fluted; fused sepals yellow-green 145A -B; lobed sepals; new petals white 155A, remaining white 155C as the petals age.

*Petal shape*.—Slightly cupped and undulation of margins weak.

*Petal texture*.—Waxy, glabrous.

*Petal dimensions*.—Similar width (7.9 mm) to length (7.4 mm).

*Stamen collar*.—Color at opening of flower yellow-green 154D.

*Stamen collar* 10 *to* 14 *days after opening of flower*.—Color yellow-green 145D.

*Gynoecium*.—1 pistil, stigma bearded, color yellow-orange 14D with style yellow-green 145D; length 7.1 mm.

*Androcoecium*.—About 10 fertile stamens with 10 infertile staminodes arranged alternatively on a collar adnate to junction of petals and calyx; filament length 1.4 mm, color white 155D aging to white 155D; staminode length 1.0 mm, color white 155D; anthers length about 0.9 mm, color greyed-orange 166B; pollen is sterile.

*Disease resistance*.—Moderate to high.

I claim:

1. A new and distinct waxflower plant substantially as shown and described herein.

* * * * *